(12) United States Patent
Akagane

(10) Patent No.: US 11,103,271 B2
(45) Date of Patent: Aug. 31, 2021

(54) MEDICAL INSTRUMENT AND MANUFACTURING METHOD OF COVERING FOR METALLIC COMPONENT

(71) Applicant: OLYMPUS CORPORATION, Hachioji (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 204 days.

(21) Appl. No.: 15/883,295

(22) Filed: Jan. 30, 2018

(65) Prior Publication Data

US 2018/0153576 A1 Jun. 7, 2018

Related U.S. Application Data

(63) Continuation of application No. PCT/JP2016/070462, filed on Jul. 11, 2016.

(30) Foreign Application Priority Data

Jul. 30, 2015 (JP) .............................. JP2015-150205

(51) Int. Cl.
*A61B 17/32* (2006.01)
*A61B 18/14* (2006.01)
*A61B 17/285* (2006.01)
*A61B 17/00* (2006.01)

(52) U.S. Cl.
CPC .... *A61B 17/320092* (2013.01); *A61B 17/285* (2013.01); *A61B 18/14* (2013.01); *A61B 2017/0084* (2013.01); *A61B 2017/0088* (2013.01); *A61B 2017/320095* (2017.08)

(58) Field of Classification Search
CPC ................... A61B 17/320068; A61B 2017/320069–320088; A61B 2018/00107–00154; A61B 2017/320074; A61B 2017/320073
See application file for complete search history.

(56) References Cited

U.S. PATENT DOCUMENTS

| 3,058,791 | A | 10/1962 | Stallman |
| 5,702,387 | A | 12/1997 | Arts et al. |
| 5,713,895 | A | 2/1998 | Lontine et al. |
| 2004/0153154 | A1 | 8/2004 | Dinkelacker |

(Continued)

FOREIGN PATENT DOCUMENTS

| CN | 101883530 A | 11/2010 |
| JP | H9-316693 A | 12/1997 |

(Continued)

OTHER PUBLICATIONS

Definition of "v-shaped", 2015, wordnik.com/words/v-shaped (Year: 2015).*
Oct. 4, 2016 International Search Report issued in International Patent Application No. PCT/JP2016/070462.
Feb. 22, 2019 Search Report issued in European Patent Application No. 16830295.8.
Mar. 6, 2019 Office Action issued in European Patent Application No. 16 830 295.8.

(Continued)

*Primary Examiner* — Katrina M Stransky
*Assistant Examiner* — Mikail A Mannan
(74) *Attorney, Agent, or Firm* — Oliff PLC

(57) ABSTRACT

A medical instrument includes: a metallic component on which a concave surface concaved with respect to a surface of the metallic component is formed; and a covering that covers the concave surface while receiving a compressive force from the concave surface of the metallic component.

12 Claims, 11 Drawing Sheets

(56) References Cited

U.S. PATENT DOCUMENTS

| | | |
|---|---|---|
| 2005/0049716 A1 | 3/2005 | Wagener et al. |
| 2008/0132887 A1 | 6/2008 | Masuda et al. |
| 2009/0143806 A1 | 6/2009 | Witt et al. |
| 2012/0029514 A1 | 2/2012 | Fairbourn et al. |
| 2013/0274736 A1* | 10/2013 | Garrison ............ A61B 18/1445 606/41 |
| 2016/0144204 A1 | 5/2016 | Akagane |

FOREIGN PATENT DOCUMENTS

| | | |
|---|---|---|
| JP | H10-500051 A | 1/1998 |
| JP | 2010-30014 A | 2/2010 |
| JP | 2011-505198 A | 2/2011 |
| WO | 2015/020147 A1 | 2/2015 |

OTHER PUBLICATIONS

Apr. 11, 2017 Office Action issued in Japanese Patent Application No. 2017-511977.

Aug. 29, 2017 Office Action issued in Japanese Patent Application No. 2017-511977.

Jan. 30, 2018 International Preliminary Report on Patentability issued in International Patent Application No. PCT/JP2016/070462.

Dec. 3, 2019 Office Action issued in Chinese Patent Application No. 201680044648.6.

Xuewei, Li, "Practical Course on Metal Material Processing," Harbin Institute of Technology Publisher, pp. 40-42, Mar. 31, 2014.

Aug. 5, 2020 Office Action issued in Chinese Patent Application No. 201680044648.6.

* cited by examiner

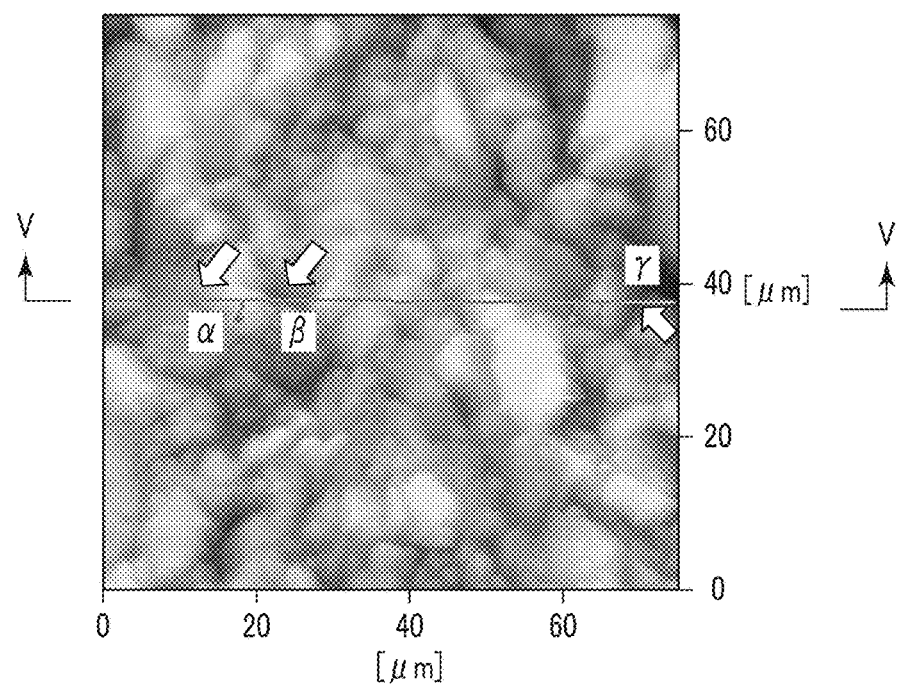
F I G. 4
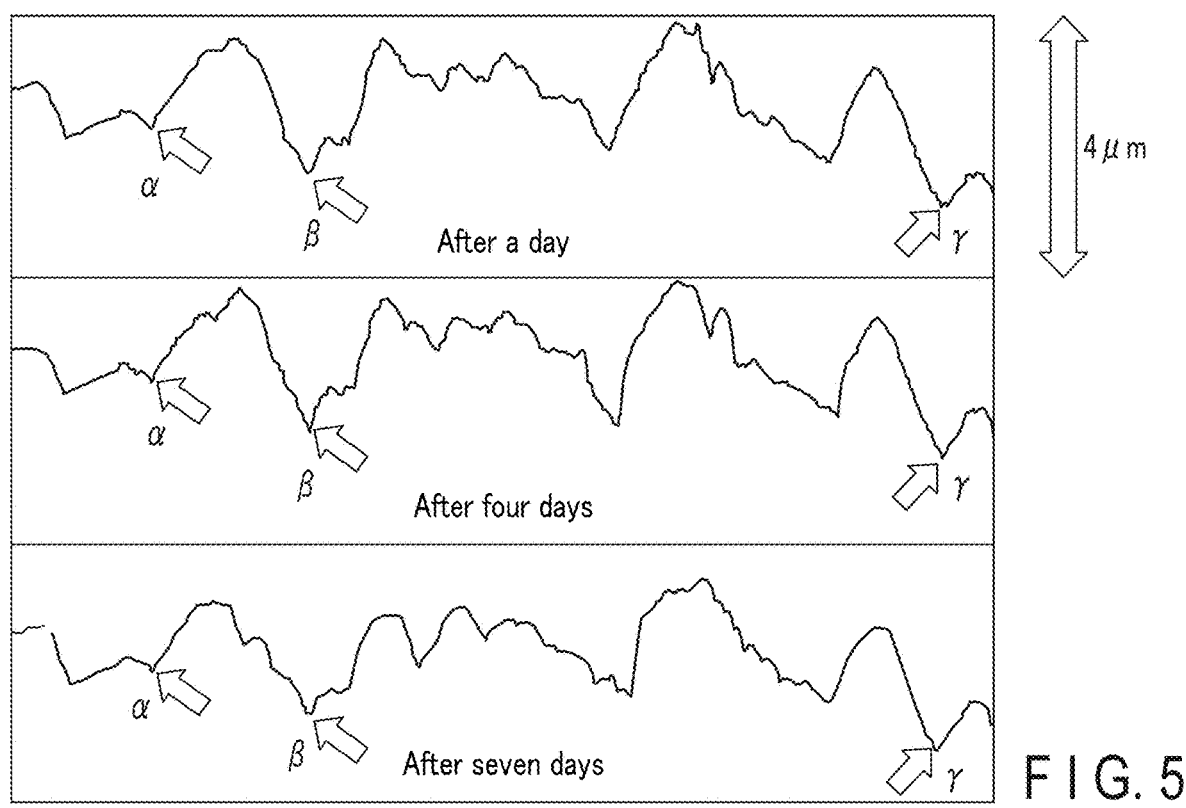
F I G. 5

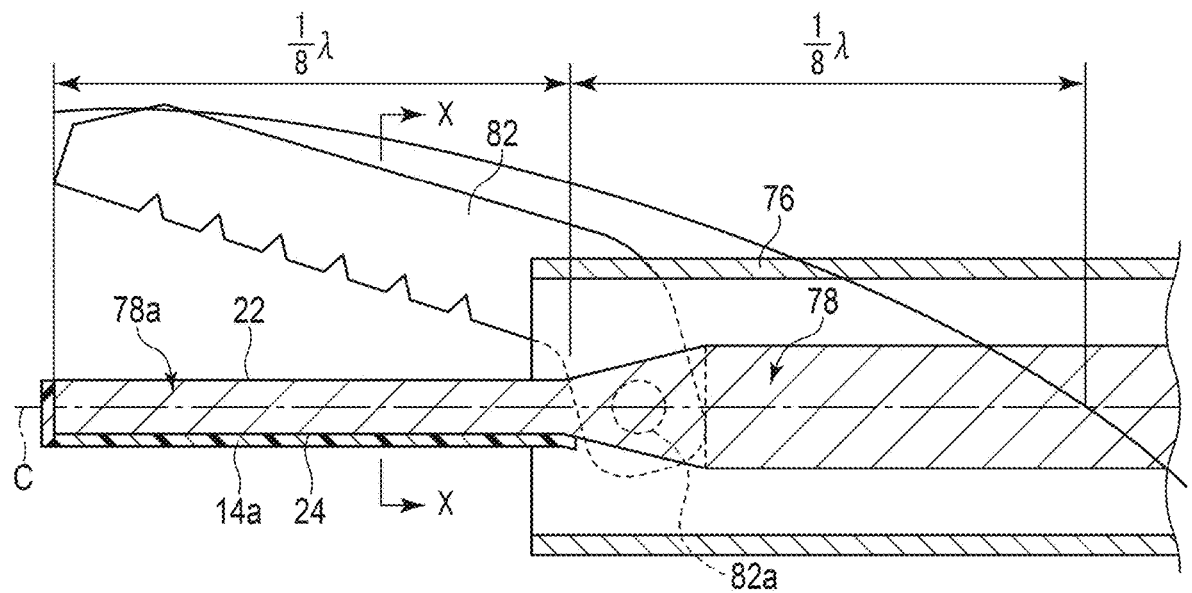
F I G. 9
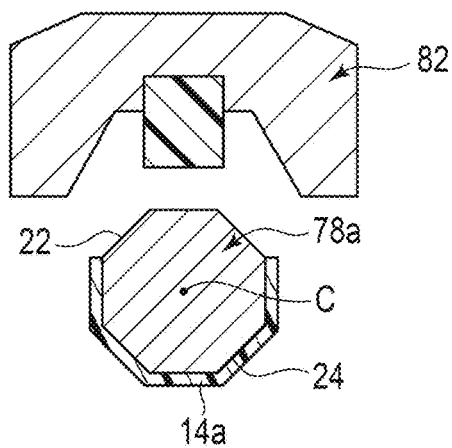
F I G. 10

MEDICAL INSTRUMENT AND MANUFACTURING METHOD OF COVERING FOR METALLIC COMPONENT

CROSS-REFERENCE TO RELATED APPLICATIONS

This application is a Continuation Application of PCT Application No. PCT/JP2016/070462, filed Jul. 11, 2016 and based upon and claiming the benefit of priority from prior Japanese Patent Application No. 2015-150205, filed Jul. 30, 2015, the entire contents of all of which are incorporated herein by reference.

BACKGROUND OF THE INVENTION

1. Field of the Invention

The present invention relates generally to a medical instrument used for various procedures, etc., and a manufacturing method of a covering for a metallic component.

2. Description of the Related Art

US 2009/143806 A1, for example, discloses applying surface processing, such as blast processing, on a surface of a metallic component, then forming a coating on the surface by a resin material. The coating is formed on, for example, a treatment section of a metallic probe used for cutting a body tissue using ultrasonic vibration. Ultrasonic vibration is transmitted to the probe, and treatment is performed by an area including the coating.

BRIEF SUMMARY OF THE INVENTION

According to one aspect of the present invention, a medical instrument includes: a metallic component on which a concave surface concaved with respect to a surface of the metallic component is formed; and a covering that covers the concave surface while receiving a compressive force from the concave surface of the metallic component.

According to the other aspect of the present invention, a manufacturing method of a covering with respect to a metallic component, includes: forming, on the metallic component comprising a surface, a concave surface on the surface by applying blast processing; and covering the concave surface by a covering material before an internal stress generated on the metallic component by forming the concave surface deforms and eliminates an opening formed on the surface by the concave surface in a manner to close the opening.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4 is an observation image obtained by an atomic force microscope showing concaves with myriads of sharp-angled dents formed by a blast media on a surface of a metallic component.

FIG. 5 is a schematic longitudinal sectional view of a same position taken along line V-V in the observation image of the atomic force microscope shown in FIG. 4 after one day, four days, and seven days from forming a concave surface of the metallic component.

FIG. 9 is a schematic longitudinal sectional view showing a proximity of a distal end portion of a probe of the treatment instrument of the example of the medical instrument according to the first embodiment.

FIG. 10 is a schematic cross-sectional view taken along line X-X in FIG. 9.

DETAILED DESCRIPTION OF THE INVENTION

Hereinafter, embodiments for implementing the present invention will be explained with reference to the drawings.

A medical instrument 10 according to a first embodiment will be explained using FIGS. 1 to 14.

Figure 1:
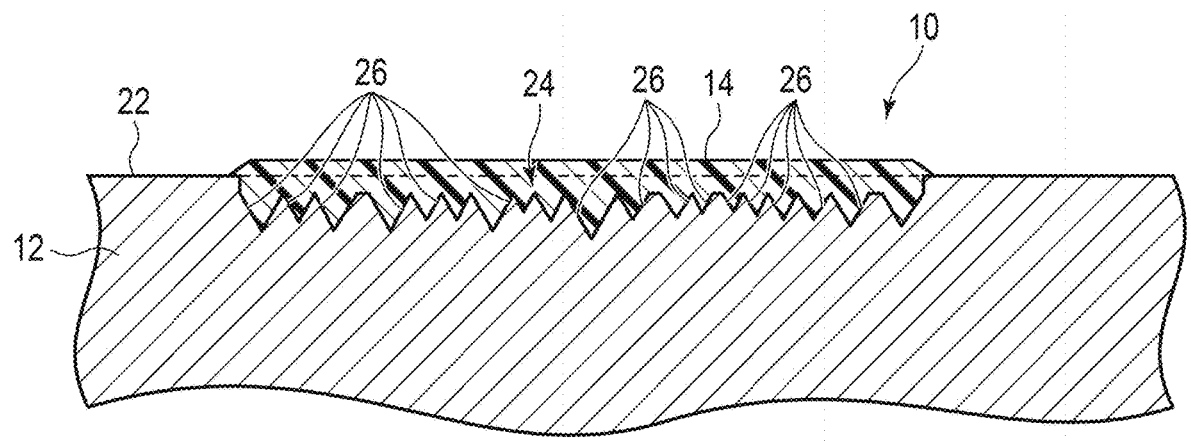
FIG. 1 is a schematic longitudinal sectional view showing a state in which a covering is formed on a metallic component used for a medical instrument according to a first embodiment.

As shown in FIG. 1, the medical instrument 10 according to the present embodiment is obtained by forming a covering (coating) 14 on at least a portion (a concave surface 24 mentioned later on) of a surface 22 of a metallic component 12 which is to be a base material. The covering 14 covers the concave surface 24 while receiving compressive forces F from the concave surface 24 of the metallic component 12. The surface 22 of the metallic component 12 may be a plane surface, or an appropriately curved surface, such as a spherical surface. Similarly, an outer surface of the covering 14 may be a plane surface, or an appropriately curved surface, such as a spherical surface.

Various kinds of metallic components 12 can be used as long as it may be used for the medical instrument 10. A material of the metallic component 12 is selected in accordance with its purpose. As the metallic component 12 used for the medical instrument 10, an appropriate metal material, such as an elastically deformable titanium alloy, stainless alloy, aluminum alloy, or a copper alloy, etc. can be used.

A material of the covering 14 (coating material) is selected in accordance with its purpose. In the present embodiment, an appropriate material that can be used as a coating material, such as a resin material, a rubber material, or a ceramic material, can be used for the covering 14. The covering 14 is not limited to use as a coating; it may also be used as an appropriate structural material for covering the metallic component 12. The purpose of forming the covering 14 is to ensure that other areas on which the covering 14 is not formed are electrically insulated from the area on which the covering 14 is formed. Other purposes of forming the covering 14 are to demonstrate heat insulating properties by preventing heat conduction from the metallic component 12 to other areas, to demonstrate water repellency and oil repellency, and to demonstrate hydrophilicity, etc. In the case of using the covering 14 that is capable of demonstrating water repellency and oil repellency, when, for example, performing a treatment that cauterizes a body tissue by applying an appropriate heat energy, the body tissue may be prevented from being stuck on the covering 14. Depending on the choice of material of the covering 14, and the setting of the coating thickness, etc., it is possible to protect the metallic component 12, and enhance the strength of the metallic component 12.

The process of forming the covering 14 on the surface of the metallic component 12 will be explained using FIG. 2A to FIG. 5. Among the processes explained here, a manufacturing process (manufacturing method) of the covering 14 with respect to the metallic component 12, in particular, can be used not only for a medical instrument.

Figure 2A:
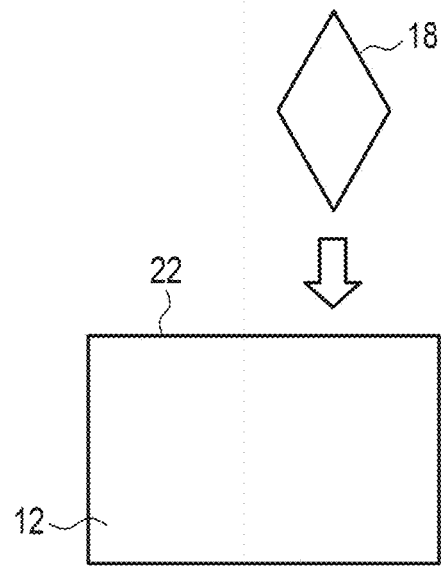
FIG. 2A is a longitudinal sectional schematic view showing a state immediately before driving a blast media into a surface of the metallic component, as a step prior to forming the covering on the metallic component used for the medical instrument according to the first embodiment.

As shown in FIG. 2A, a blast media 18 for blast processing is prepared in order to perform surface processing on a part of or entirely on the surface 22 of the metallic component 12. For the blast media 18, for example, an alundum which is a kind of alumina, a carborundum which is a kind of silicon carbide, and a garnet having a sharp portion, etc. and being capable of forming a sharp-angled dent on the surface 22 of the metallic component 12, are used. The blast media 18 that includes, for example, a grain size of about No. 180, and using a media having a finer grain size, in particular, a grain size of at least No. 220, is preferred. The depth of the dent 26 mentioned later on made by each of the blast medium 18 is preferably set to, for example, approximately less than 1 µm to approximately several micrometers; however, the depth may be deeper or shallower than this. Here, a spherical blast media is not used against the surface 22 of the metallic component 12. Furthermore, surface processing by etching against the surface 22 of the metallic component 12 is also not possible.

Here, FIG. 2A to FIG. 3C show a series of processing when forming the covering 14 on the metallic component 12. In the case of forming the covering 14 on a part of the surface 22 of the metallic component 12, publicly-known appropriate masking processing should be applied around an area on which the covering 14 is desired to be formed, that is, around an area on which the concave surface 24 is desired to be formed, for protection.

Figure 2B:
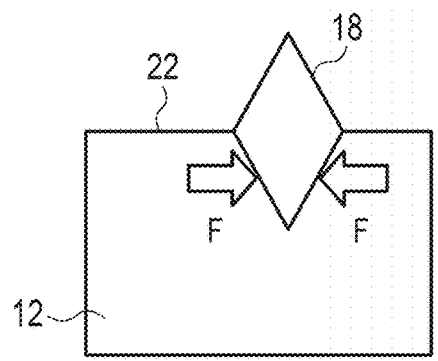
FIG. 2B is a longitudinal sectional schematic view showing a state in which the blast media is driven into the surface of the metallic component, and a sharp-angled dent is formed to the metallic component by the blast media, as a step prior to forming the covering on the metallic component used for the medical instrument according to the first embodiment.
Figure 2C:
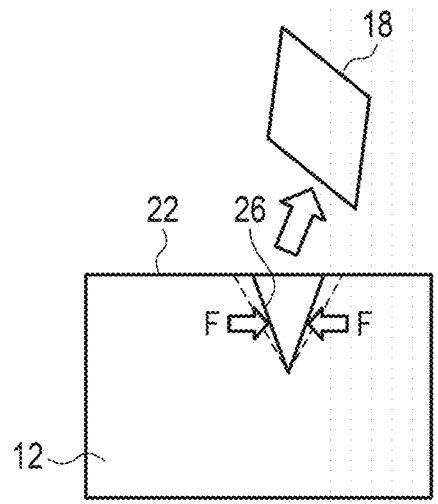
FIG. 2C is a longitudinal sectional schematic view showing a state in which the dent has become slightly smaller than the blast media by a spring back at the same time as when the blast media that has formed the sharp-angled dent on the surface of the metallic component has fallen off from the metallic component, as a step prior to forming the covering on the metallic component used for the medical instrument according to the first embodiment.
Figure 3A:
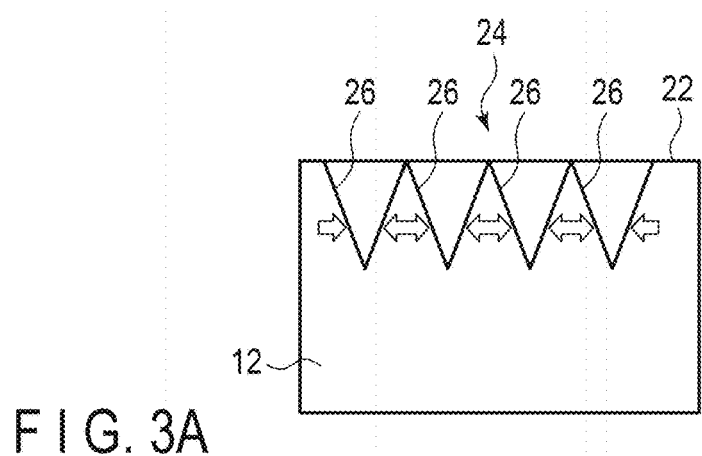
FIG. 3A is a schematic longitudinal sectional view showing a state immediately after forming a concave surface by myriads of sharp-angled dents by the blast media shown in FIGS. 2A to 2C, as a step prior to forming the covering on the metallic component used for the medical instrument according to the first embodiment.
Figure 3B:
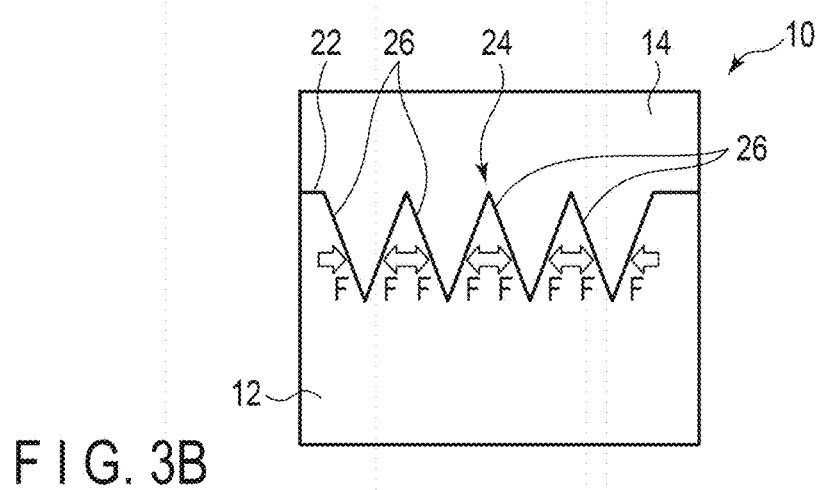
FIG. 3B is a schematic longitudinal sectional view showing a state in which the covering is formed on the metallic component used for the medical instrument in a state where a deformation amount with respect to a shape of the myriads of dents shown in FIG. 3A is small in the medical instrument according to the first embodiment.
Figure 3C:
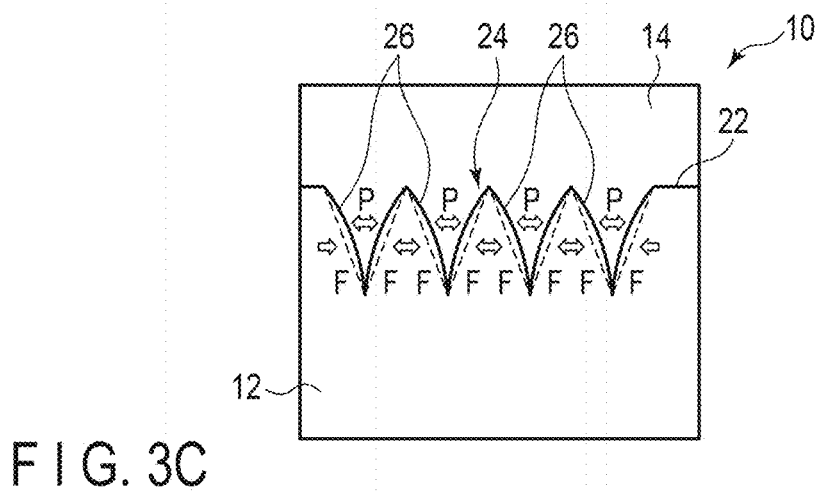
FIG. 3C is a schematic longitudinal sectional view showing a state in which each of the myriads of dents formed on the metallic component used for the medical instrument is deformed from the state shown in FIG. 3B, and a clutching force is exerted on the covering in the medical instrument according to the first embodiment.

As shown in FIG. 2A to FIG. 2C and FIG. 3A, the blast media 18 is collided against the surface 22 of the metallic component 12 by the publicly-known blast processing using the above-mentioned blast media 18. Concavities and convexities are formed on the surface 22 of the metallic component 12 by myriads of dents. Therefore, on the surface 22 of the metallic component 12, a concave surface (coating region) 24 having myriads of concaved dents 26 is created. Here, as shown in FIG. 3A and FIG. 4, the concave surface 24 with myriads of dents 26 is formed on a predetermined area on the surface 22 of the metallic component 12, and the blast media 18 falls off from the concave surface 24 of the metallic component 12. By using alundum, carborundum, and garnet, etc. as the blast media 18, when forming the concave surface 24 on the surface 22 of the metallic component 12, an approximately V-shaped sharp-angled dent can be formed on its longitudinal-section surface. On the concave surface 24, myriads of dents 26 with a depth of, for example, 1 µm or smaller to approximately several micrometers are formed.

As shown in FIG. 2B and FIG. 2C, when the blast media 18 is collided against the surface 22 of the metallic component 12 to form the concave surface 24, that is, the myriads of dents 26, internal stress F is accumulated in the metallic component 12 as an elastic body, which instantaneously causes a springback. Therefore, the metallic component 12 that acts as an elastic body deforms an opening formed by each of the dents 26 to be closed, and attempts to narrow the opening.

Here, FIG. 5 shows a shape of a cross-sectional surface at a same position after one day, four days, and seven days of forming the concave surface 24 on the surface 22 of the metallic component 12, which can be observed by, for example, an atomic force microscope. A position denoted by symbol α in FIG. 4 corresponds to a position denoted by symbol α in FIG. 5, a position denoted by symbol β in FIG. 4 corresponds to a position denoted by symbol β in FIG. 5, and a position denoted by symbol γ in FIG. 4 corresponds to a position denoted by symbol γ in FIG. 5.

When forming the concave surface 24 on the metallic component 12 by the blast media 18 as shown in FIG. 2B, myriads of dents 26 with a depth of 1 µm or smaller to approximately several micrometers are formed as shown in FIG. 4 and FIG. 5.

Figure 2D:
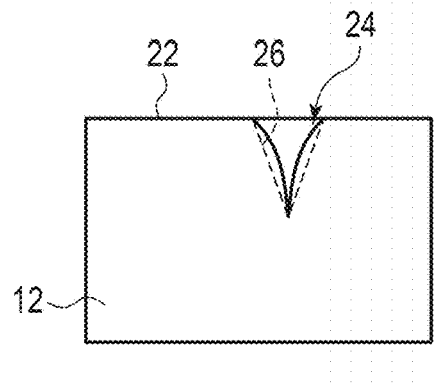
FIG. 2D is a longitudinal sectional schematic view showing a state of the dent after a few days of forming the sharp-angled dent on the surface of the metallic component by the blast media, as a step prior to forming the covering on the metallic component used for the medical instrument according to the first embodiment.

The dents 26 of the concave surface 24 on the surface 22 of the metallic component 12 deform from the state shown in FIG. 2C to the state shown in FIG. 2D by the internal stress F in the course of time. Here, as time progresses, the metallic component 12 releases the internal stress F of each of the dents 26 of the concave surface 24.

After the blast media 18 is collided against the surface 22 of the metallic component 12 to form the concave surface 24 by a sharp-angled dent, a material (here, for example, a PEEK material will be used) that forms the covering 14 is applied to the concave surface 24. Here, since myriads of dents 26 are formed on the concave surface 24 by the blast processing, the material forming the covering 14 comes in contact with each surface formed by the myriads of dents 26 on the concave surface 24. Subsequently, the material forming the covering 14 is heated up (baked) to a predetermined curing temperature, and the process of forming the covering 14 on the concave surface 24 is ended. Therefore, a resin material (for example, a PEEK material) is formed as the covering 14.

After the covering 14 is formed on the concave surface 24 of the metallic component 12, along with the release of the internal stress F of each of the dents 26 on the concave surface 24, a myriad of deformations in nanometers occur on each of the dents 26. Here, each of the dents 26 is deformed to release the internal stress F by narrowing the distance between surfaces that face each other, etc. Therefore, the clutching force (compressive force) P for holding the covering 14 by the myriads of dents 26 on the concave surface 24 increases as the stress release progresses.

A spherical blast media, such as glass beads, is unsuitable for the blast processing for forming the concave surface in the present embodiment. This is because a shot of myriads of spherical glass beads would produce an almost planar concave surface, and would not form a sharp-angled dent. In other words, it would be difficult for a spherical blast media to provide a clutching force on the coating.

Here, a method of measuring adhesion strength of the covering 14 with respect to the metallic component 12 will be explained.

Figure 6A:
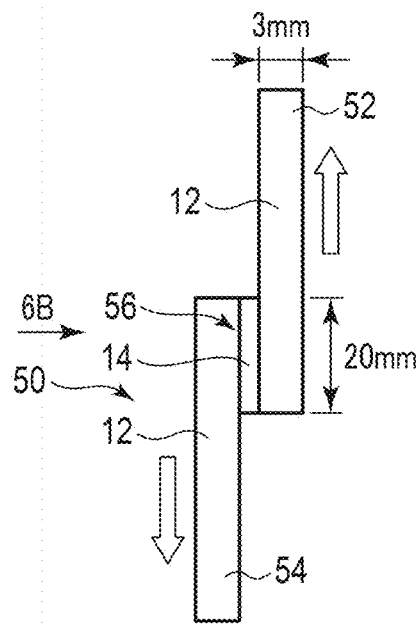
FIG. 6A is a schematic view showing a test specimen for measuring peel-ability (adhesion) of the covering (adhesion part) in accordance with the number of days from forming the concave surface until forming the covering.
Figure 6B:
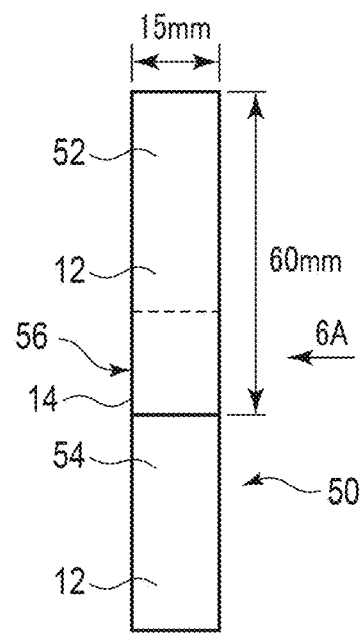
FIG. 6B is a schematic view showing a state in which the test specimen in FIG. 6A is observed from a direction of arrow 6B in FIG. 6A.

As shown in FIG. 6A and FIG. 6B, a test specimen 50 for tensile testing is prepared. The test specimen 50 includes a first plate member 52 and a second plate member 54. For example, each of the first plate member 52 and the second plate member 54 is a plate with a height of 60 mm, a width of 15 mm, and a thickness of 3 mm. The first plate member 52 and the second plate member 54 are prepared, and the concave surface 24 (see FIG. 2A and FIG. 2C) is formed simultaneously in a predetermined range by the blast media 18. The concave surface 24 is formed in the range of a height of 20 mm and a width of 15 mm including end portions along a longitudinal direction of the first plate member 52 and the second plate member 54. Subsequently, the material of the covering 14 is applied to the concave surface 24, and comes in contact with the myriads of dents 26 on the concave surface 24. The test specimen 50 including an adhesion part 56 is created by facing the concave surfaces 24 to each other, bonding the first plate member 52 and the second plate member 54 together, and setting the material of the coating 14 to an appropriate temperature. Since the adhesion part 56 corresponds to the covering 14, the strength of the adhesion part 56 can be considered as being the strength of the covering 14. In this manner, the adhesion part 56 allows the first plate member 52 and the second plate member 54 to be bonded together. Therefore, the covering 14 that is formed using the technique explained herein is not limited to serve as a coating, and can be used as an adhesive agent for bonding the metallic components 12 together. Here, a PEEK material that is widely used as a so-called engineering plastic will be used as the covering 14.

In order to compare adhesion, for example, five test specimens 50 are prepared. The concave surface 24 is simultaneously formed on the first plate member 52 and the second plate member 54 of the five test specimens 50. Here, FIG. 5 shows a cross-sectional surface shape taken along line V-V in FIG. 4 by the atomic force microscope. The release of the internal stress F causes an opening angle of the almost V-shaped dent 26 on the concave surface 24 to become slightly smaller after four days than after one day, and slightly smaller after seven days than after four days. Furthermore, the angle of the area on which the dent is formed changes gradually from a sharp state to a smooth state.

After one day, two days, three days, seven days, and fourteen days from when the concave surface 24 is formed, the covering 14 is formed respectively in the manner mentioned above to complete the test specimen 50. The material and condition for forming the covering 14 are the same. The covering 14 is formed on the test specimen 50 completed after one day, the test specimen 50 completed after two days, the test specimen 50 completed after three days, the test specimen 50 completed after seven days, and the test specimen 50 completed after fourteen days from when the concave surface 24 is formed, by applying the same PEEK material in the same thickness. The adhesion part 56 of each of the test specimens 50 is the same dimension. Tensile testing is then performed immediately after each of the test specimens 50 is created.

Regarding the plurality of test specimens 50, the first plate member 52 and the second plate member 54 are pulled at a constant speed in a state where the first plate member 52 and the second plate member 54 are adhered via the adhesion part 56. A load of when the adhesion part 56 is destroyed and the first plate member 52 and the second plate member 54 come apart is considered as the adhesion strength. For each of the test specimens 50, the tensile testing is performed in the same manner to obtain the adhesion strength thereof, respectively.

Figure 7:
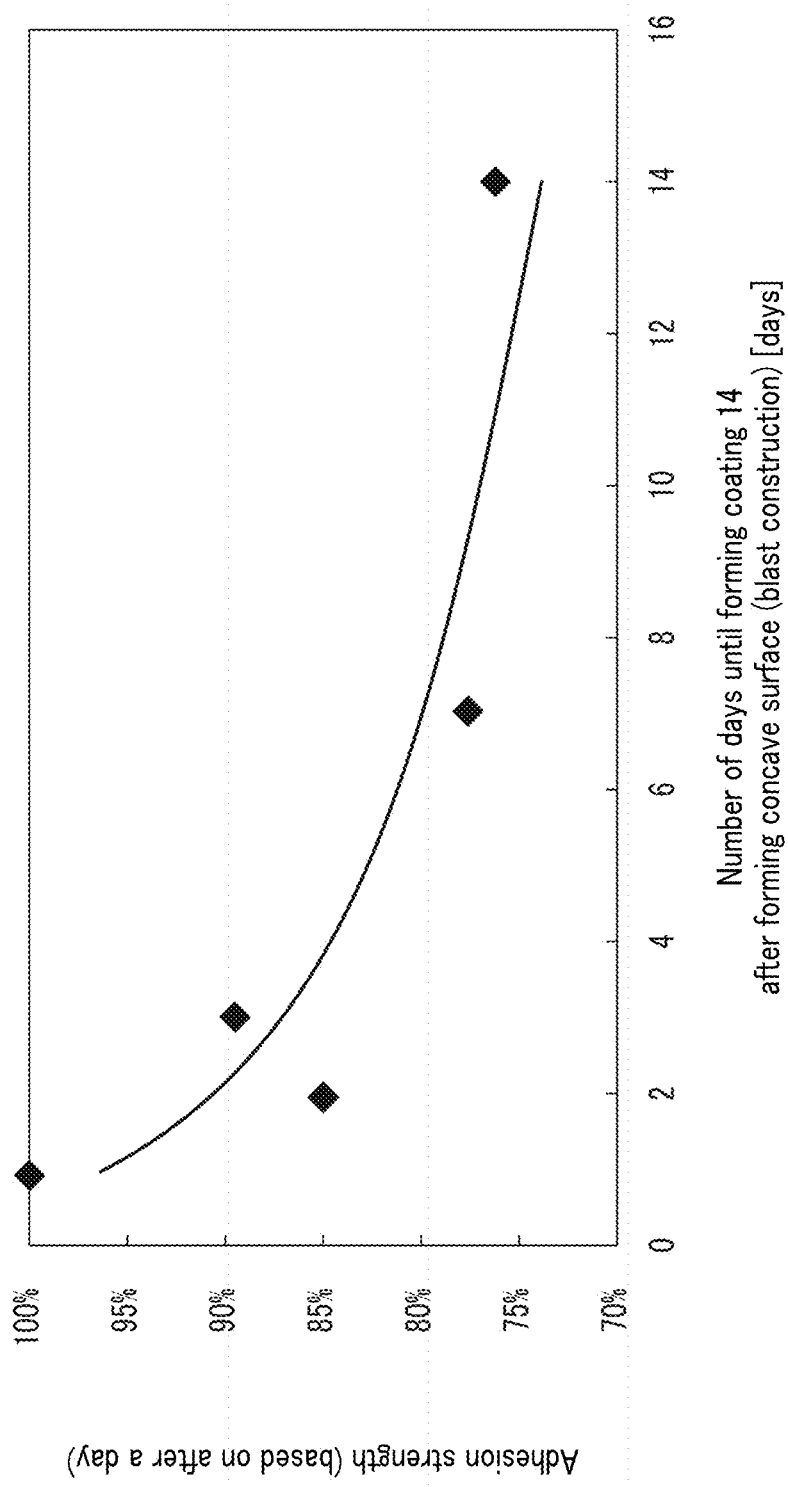
FIG. 7 is a graph showing a result of tensile testing the test specimen shown in FIG. 6A and FIG. 6B under an appropriate condition, in which a horizontal axis shows the number of days that have passed since forming the concave surface on the metallic component until forming the covering, and a vertical axis shows, when considering the covering formed after one day of forming the concave surface as 100%, the peel-ability (adhesion) of when the covering (adhesion part) is formed after two days, three days, seven days, and fourteen days of forming the concave surface.

FIG. 7 shows changes in the adhesion strength of the test result of the test specimen 50 on which the covering 14 is formed after two days, three days, seven days, and fourteen days, when considering the adhesion strength that is the test result of the test specimen 50 on which the covering 14 is formed one day after forming the concave surface 24 as 100%.

Among the test results of the five test specimens 50, the test specimen 50 on which the coating 14 is formed after one day from forming the concave surface 24 has the highest adhesion strength. The test specimens 50 on which the covering 14 is formed after two days and three days from forming the concave surface 24 have an approximately 10% decreased adhesion strength compared to the test specimen 50 on which the covering 14 is formed after one day from forming the concave surface 24. The test specimens 50 on which the covering 14 is formed after seven days and fourteen days from forming the concave surface 24 have an approximately 20% decreased adhesion strength compared to the test specimen 50 on which the covering 14 is formed after one day from forming the concave surface 24.

The decrease in the adhesion strength of the test specimens 50 with respect to the passage of time from forming the concave surface 24 will be considered. The test specimens 50 on which the covering 14 is formed after seven days and fourteen days from forming the concave surface 24, and the test specimens 50 on which the covering 14 is formed after two days and three days from forming the concave surface 24, are compared with the decrease in the adhesion strength of the test specimen 50 on which the covering 14 is formed after one day from forming the concave surface 24. Here, it may be recognized that the decrease in strength becomes milder as time progresses.

In any case, the adhesion strength between the metallic component 12 and the covering 14 tends to decrease as time progresses after the concave surface 24 is formed. Therefore, after the concave surface 24 is formed, by arranging the covering 14 on the concave surface 24 within a couple of days, or, if possible, on the same day, a higher adhesion strength can be obtained. This was a result of the inventor of the present invention discovering, while working hard to improve the endurance of the covering 14 with respect to the metallic component 12, that the covering 14 that excels in endurance with respect to the metallic component 12 would be obtained by forming the covering 14 on the metallic component 12 as promptly as possible after the concave surface 24 with myriads of dents 26 is formed. In other words, the inventor of the present invention discovered that the covering 14 will excel in endurance with respect to the metallic component 12 if the concave surface 24 is coated by the coating material before the internal stress F occurring in the metallic component 12 by forming the concave surface 24 on the surface 22 of the metallic component 12 deforms and vanishes the opening of the dent 26 formed on the surface 22 by the concave surface 24, in a manner to close the opening. The sooner the covering 14 is formed after the concave surface 24 is formed on the metallic component 12, the higher the adhesion becomes when the covering 14 covers the concave surface 24 while receiving the clutching force (compressive force) P from the concave surface 24 of the metallic component 12. Therefore, by forming the covering 14 as soon as possible after the concave surface 24 is formed on the metallic component 12, even if an external force is applied to the covering 14, the endurance with respect to the external force will improve, thereby preventing the covering 14 from peeling off from the metallic component 12.

Sometimes, a processor of the metal material for performing blast processing on the metallic component 12 and a processor of the resin material that forms the coating 14 on the metallic component are different. Therefore, it took at least, for example, about two to three days to form the covering 14 on the concave surface 24 after the concave surface 24 was formed on the surface 22 of the metallic component 12. However, as explained in the present embodiment, a higher adhesion strength can be obtained even by using the same material if the period until forming the covering 14 on the concave surface 24 is preferably within the same day, or is about one day after the concave surface 24 is formed on the surface 22 of the metallic component 12.

The relationship between the above-mentioned metallic component 12 and covering 14 may be used for the metallic component 12 of the medical instrument 10. In the medical instrument 10 according to the present embodiment, an example of forming the covering 14 on a portion where a higher adhesion strength is required between the covering 14 and the metallic component 12, preferably within one day from when the concave surface 24 is formed, that is, in which the adhesion of the covering 14 with respect to the metallic component 12 is enhanced as much as possible, will be explained.

As the medical instrument 10, an example of a treatment instrument 70 shown, for example, in FIG. 8 that uses ultrasonic vibration to dissect, etc. a body tissue, will be explained. Since the structure of the treatment instrument 70 is publicly-known, here, a simple explanation will be provided. Detailed explanations will be omitted.

Figure 8:
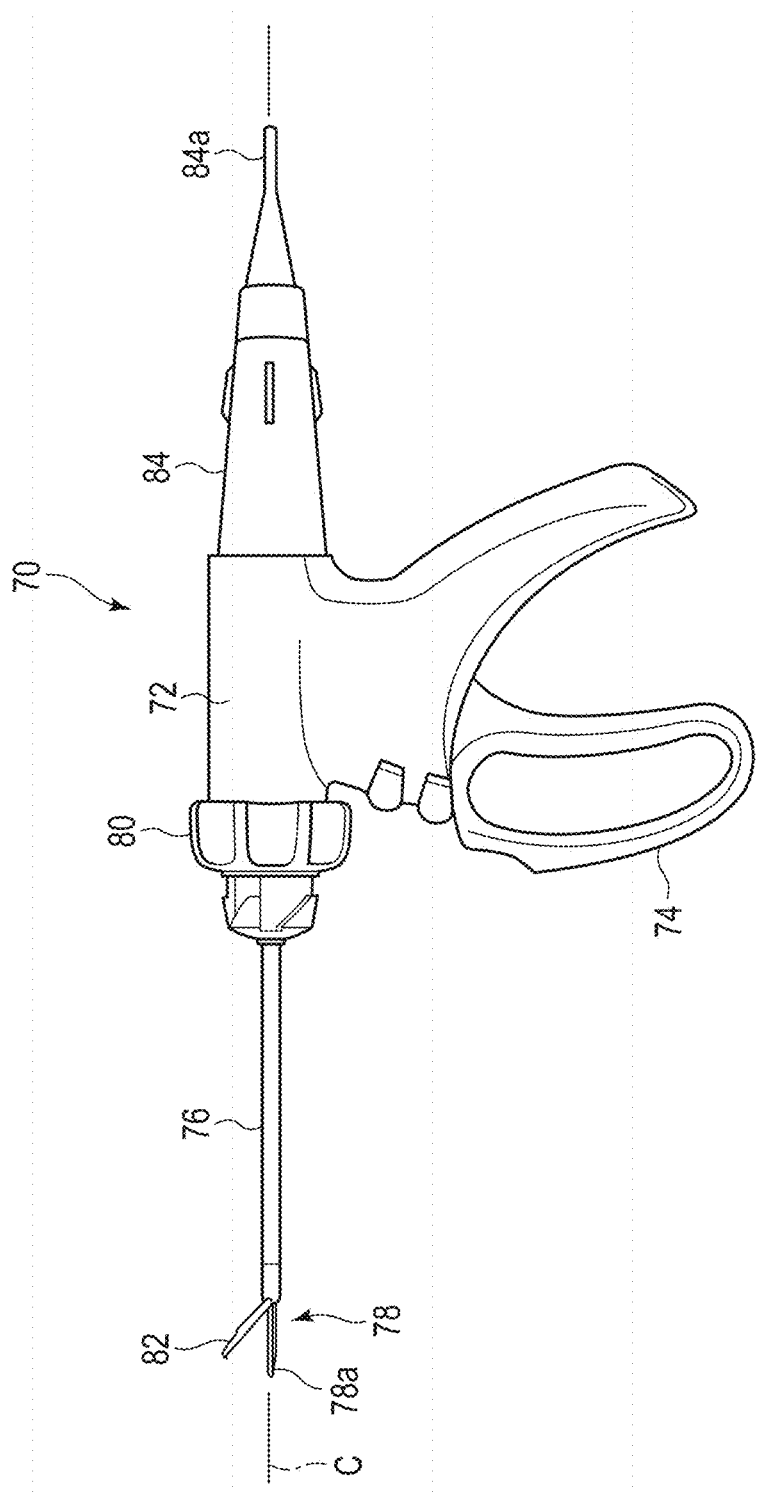
FIG. 8 is a schematic view showing a treatment instrument of an example of the medical instrument according to the first embodiment.

As shown in FIG. 8, the treatment instrument 70 comprises a main body 72 including a handle 74, a cylindrical sheath 76 arranged on the main body 72, a probe 78 inserted within the sheath 76 and arranged on the main body 72, and a knob 80 that is arranged on the main body 72 and rotates the sheath 76 and the probe 78 around a longitudinal axis C. A jaw 82 is arranged on the distal end side of the sheath 76, and is openable and closable by a revolving axis 82a (see FIG. 9) with respect to a treatment section 78a on the distal end side of the probe 78 by operating the handle 74. An ultrasonic vibrator unit 84 that generates ultrasonic vibration is attached on the opposite side of where the sheath 76 is arranged on main body 72. When the ultrasonic vibrator unit 84 is attached to the main body 72, the proximal end of the probe 78 is connected to the ultrasonic vibrator unit 84.

The longitudinal axis C extends from the distal end portion to the proximal end portion of the treatment instrument 70. The longitudinal axis C is defined by the main body 72, the sheath 76, the probe 78, the knob 80, and the ultrasonic vibrator unit 84.

Here, as the metallic component 12, an example of a publicly-known probe 78 that transmits ultrasonic vibration from the ultrasonic vibrator unit 84 will be explained. For the probe 78, a titanium alloy material, for example, is used as the metallic component 12. The probe 78 that is obtained by forming the covering 14 within a day after forming the concave surface 24 on the metallic component 12 is used. For the covering 14, for example, a PEEK material is used. The covering 14 of the probe 78 is preferably configured by a material that has heat insulating properties. The covering 14 is preferably configured by a material that has electrical insulating properties. The covering 14 is preferably configured by a water repellent and/or oil repellent material.

Since the probe 78 is publicly-known, detailed explanations will be omitted. The treatment section 78a of the probe 78 faces the jaw 82 of the treatment instrument 70 shown in FIG. 9. A body tissue is dissected by the treatment section 78a of the probe 78 on the basis that the body tissue is clamped between the treatment section 78a of the probe 78 and the jaw 82 and the ultrasonic vibration is transmitted from the proximal end to the distal end of the probe 78.

As shown in FIG. 9 and FIG. 10, the covering 14 is, for example, formed at a position denoted by symbol 14a on the treatment section 78a of the titanium alloy-made probe 78. The coating 14 is formed on an area on the opposite side of the jaw 82 on the treatment section 78a of the probe 78. In other words, here, the covering 14 is formed at a position isolated from the jaw 82 on the rod-like treatment section 78a of the probe 78, and not at a position adjacent to the jaw 82.

The length of the probe 78 can be determined in relation to an oscillating frequency generated by a piezoelectric element (electrical element) 92 (see FIG. 13) of the ultrasonic vibrator unit 84. The distal end of the probe 78 is set to an anti-node position of the vibration. The covering 14 is preferably formed at a region of ¼ of a wavelength from the distal end of the probe 78 on the treatment section 78a of the probe 78. The coating 14 in particular is preferably formed at a region of ⅛ of a wavelength from the distal end of the probe 78.

On the treatment section 78a of the probe 78, frictional heat caused by the vibration transmitted to the probe 78 occurs between a position of the treatment section 78a adjacent to the jaw 82 and the body tissue. In this manner, the body tissue is dissected by the frictional heat. Furthermore, in the case where the jaw 82 and a position on the treatment section 78a of the probe 78 that is adjacent to the jaw 82 and that does not form the covering 14 each form a high-frequency electrode, when the body tissue clamped between the treatment section 78a of the probe 78 and the jaw 82 is treated by Joule heat, the clamped body tissue coagulates, and, if the body tissue is a blood vessel, bleeding is stopped. Therefore, the body tissue can be dissected while reliably stopping bleeding. This treatment instrument 70 can also perform only the treatment for stopping bleeding without oscillating the ultrasonic vibration.

Here, the above-mentioned technique is used between the treatment section 78a of the probe 78 of the metallic component 12 and the coating 14 denoted by symbol 14a. Therefore, the covering 14 is also prevented from peeling off from the metallic component 12 when the body tissue is treated in a state where the ultrasonic vibration is transmitted to the probe 78 in a case where, for example, the treatment section 78a of the probe 78 is placed in a liquid such as saline.

As shown in FIG. 9, depending on the material used for the coating 14, the coating 14 may also be formed on a surface (cavitation generating surface) perpendicular to a vibrating direction on the distal end of the probe 78. Also, in this case, the coating 14 may be prevented from being peeled off by a shearing action.

Figure 11:
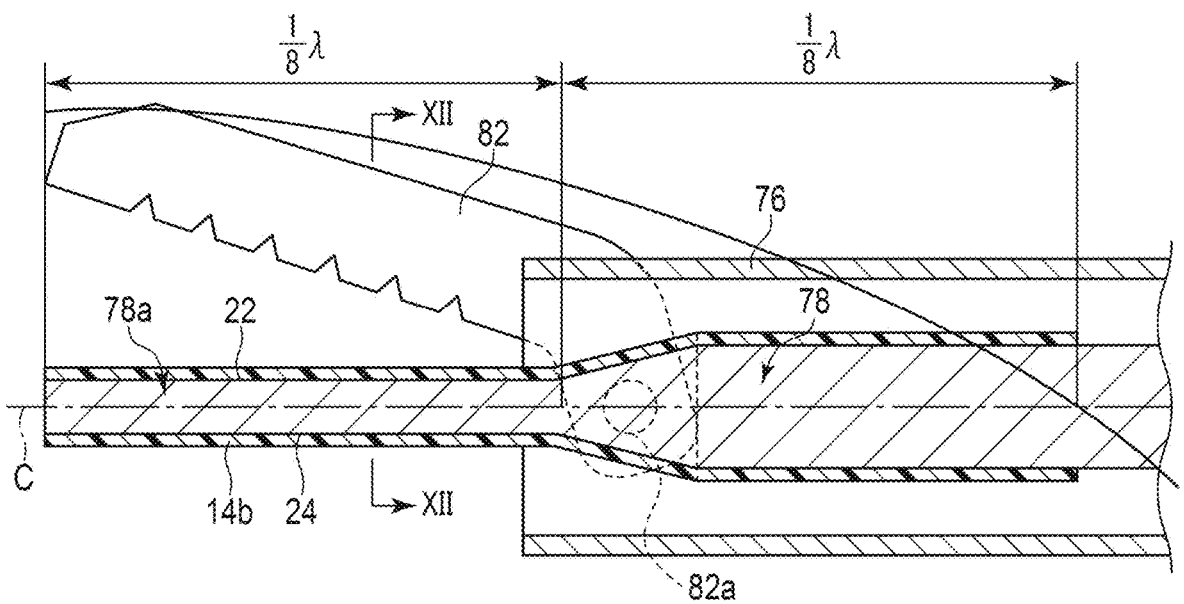
FIG. 11 is a schematic longitudinal sectional view showing a proximity of the distal end portion of the probe of the treatment instrument of the example of the medical instrument according to the first embodiment.
Figure 12:
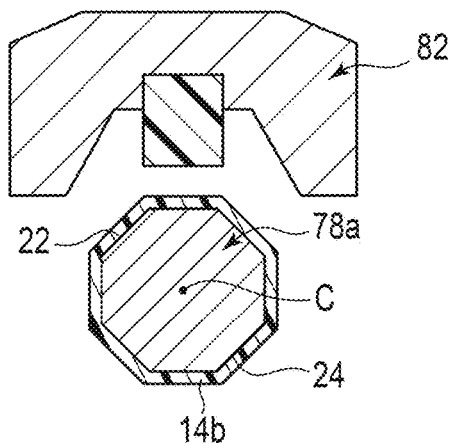
FIG. 12 is a schematic cross-sectional view taken along line XII-XII in FIG. 11.

In the examples shown in FIG. 11 and FIG. 12, the covering 14 is, for example, formed at a position denoted by symbol 14b on the treatment section 78a of the titanium alloy-made probe 78. Here, the covering 14 is formed on both a position separated from the jaw 82 and a position adjacent to the jaw 82 on the rod-like treatment section 78a of the probe 78. In other words, the coating 14 is formed on the entire circumference of an outer periphery surface in a circumferential direction with respect to the longitudinal axis C of the rod-like treatment section 78a of the probe 78. Here, as an example, the covering 14 is formed at a region of ¼ of a wavelength from the distal end of the probe 78.

On the treatment section 78a of the probe 78, frictional heat caused by the vibration transmitted to the probe 78 occurs between the coating 14 and the body tissue. In this manner, the body tissue is dissected by the frictional heat. The covering 14 of the probe 78 maintains a state where the clutching force P from the concave surface 24 is exerted by the internal stress (compressive force) F of the metallic component 12 made of titanium alloy. Therefore, even by friction, the covering 14 is prevented from being peeled off from the concave surface 24 of the metallic component 12. Accordingly, even in a state where the covering 14 formed on the probe 78 comes in contact with the body tissue held between the covering 14 and the jaw 82, by transmitting an appropriate ultrasonic vibration to the probe 78, a treatment such as dissection, etc. may be performed by the ultrasonic vibration.

Here, the above-mentioned technique is used between the treatment section 78a of the probe 78 of the metallic component 12 and the covering 14 denoted by symbol 14b. Therefore, the coating 14 may also be prevented from peeling off from the metallic component 12 when the body tissue undergoes treatment such as dissection in a state where the ultrasonic vibration is transmitted to the probe 78 in a state where, for example, the treatment section 78a of the probe 78 is placed in liquid such as saline.

Since the coating 14 is coated on the entire circumference around the longitudinal axis C of the probe 78, and the coating is prevented from peeling off, electric insulation can be ensured by the coating 14. Therefore, even in a case of using the treatment instrument 70 in combination with, for example, a monopolar-type high frequency treatment instrument (unillustrated), electricity from other high frequency treatment instruments may be prevented from being supplied to the probe 78. However, since the coating 14 denoted by symbol 14b is formed on the entire circumference, the treatment section 78a of the probe 78 cannot be used as an electrode. Therefore, the hemostatic performance of the treatment instrument 70 declines in comparison to the treatment instrument shown in FIG. 9 and FIG. 10.

Figure 13:
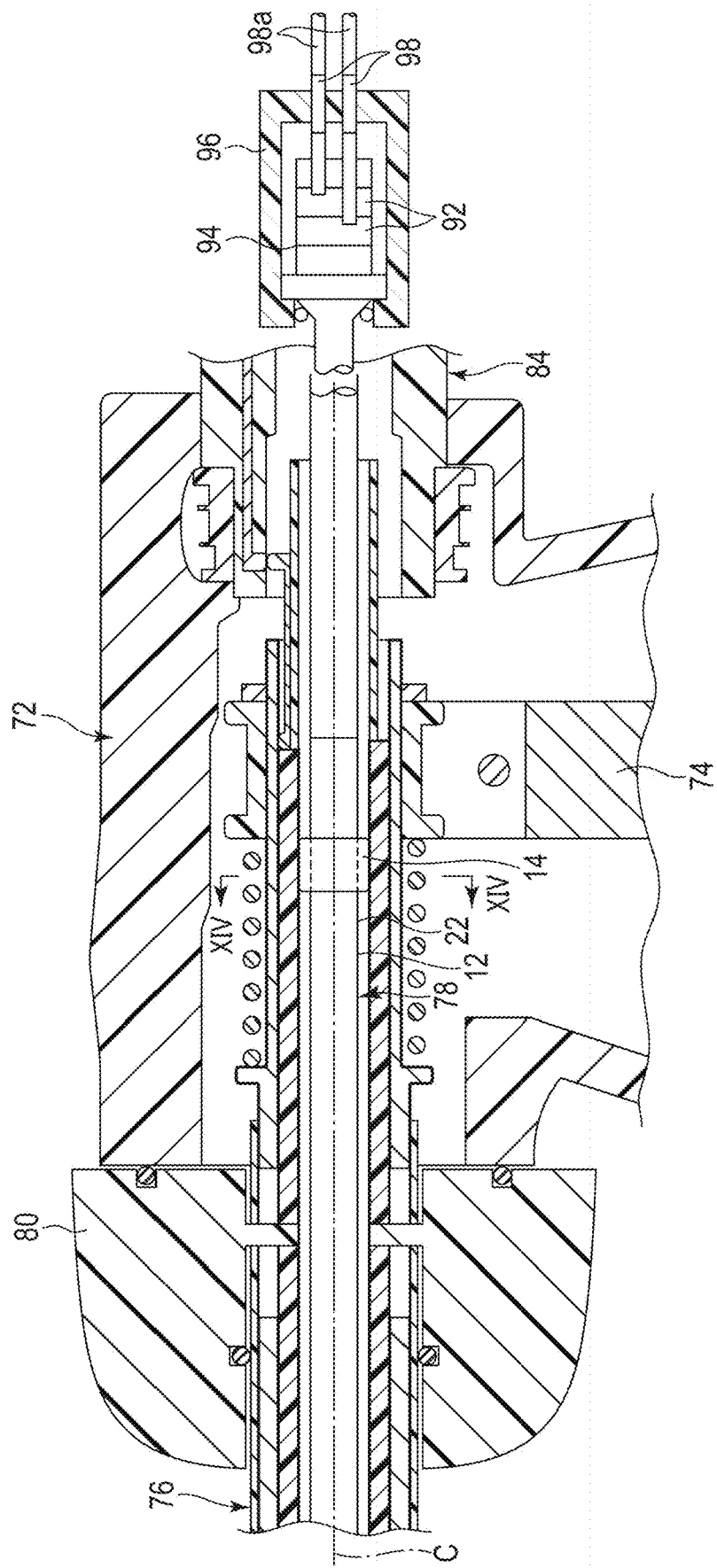
FIG. 13 is a schematic longitudinal sectional view showing a main body of the treatment instrument of the example of the medical instrument according to the first embodiment.
Figure 14:
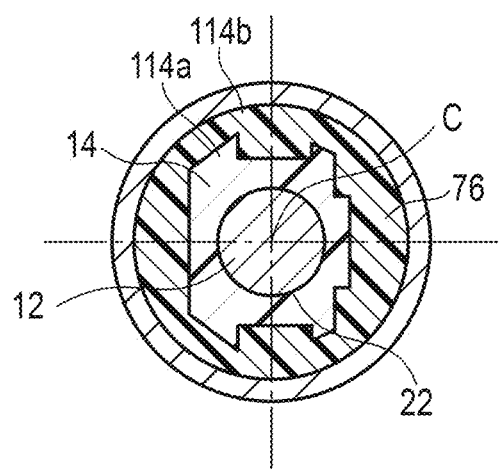
FIG. 14 is a schematic cross-sectional view taken along line XIV-XIV in FIG. 13.

As shown in FIG. 13, the knob 80 that rotates the sheath 76 and the probe 78 around the longitudinal axis C is arranged on the distal end of the main body 72 of the treatment instrument 70. Since this is a publicly-known structure, details will be omitted; however, when the knob 80 is rotated around the longitudinal axis C, the probe 78 and the sheath 76 are rotated in the same direction as the rotation of the knob 80. As shown in FIG. 14, the coating 14 made of a resin material that has electrical insulating properties is formed on the outer periphery surface of the proximal end portion of the probe 78. An outer rim of the coating 14 is formed in an appropriate shape other than a circular form.

Here, when the knob 80 is rotated around the longitudinal axis of the probe 78, the rotation is transmitted to the probe 78 via the coating 14. Therefore, the probe 78 also rotates around the longitudinal axis interlocking with the rotation of the knob 80. Here, the above-mentioned relationship between the metallic component 12 and the covering 14 is used for the probe 78 and the coating 14. Therefore, even when a rotation torque is applied to the covering 14 by the rotation of the knob 80, the covering 14 maintains a state where it is coated on the probe 78 without being peeled off. Accordingly, the rotation of the knob 80 can be transmitted to the probe 78 through the covering 14. Therefore, the covering 14 gives/receives to/from the knob 80 the rotation torque that rotates the probe 78 around the longitudinal axis C. The coating 14 is preferably formed of a material that has electrical insulation properties and is tolerant to the rotation torque, such as a PEEK material, etc.

Now, a second embodiment will be explained using FIG. 15. The present embodiment is a modified example of the first embodiment, in which, to omit detailed explanations, the same symbols as those in the first embodiment will be applied whenever possible to the same members or the members with the same functions as those explained in the first embodiment.

Generally, it is said that even if a metal material and a resin material are adhered together, it would be difficult to achieve an adhesion as that achieved between resin materials. However, by using the process explained in the first embodiment, the adhesion at an interface between the metallic component 12 which, for example, is a titanium alloy material, and the coating 14 of a resin material which is, for example, a PEEK material, can be improved.

Figure 15:
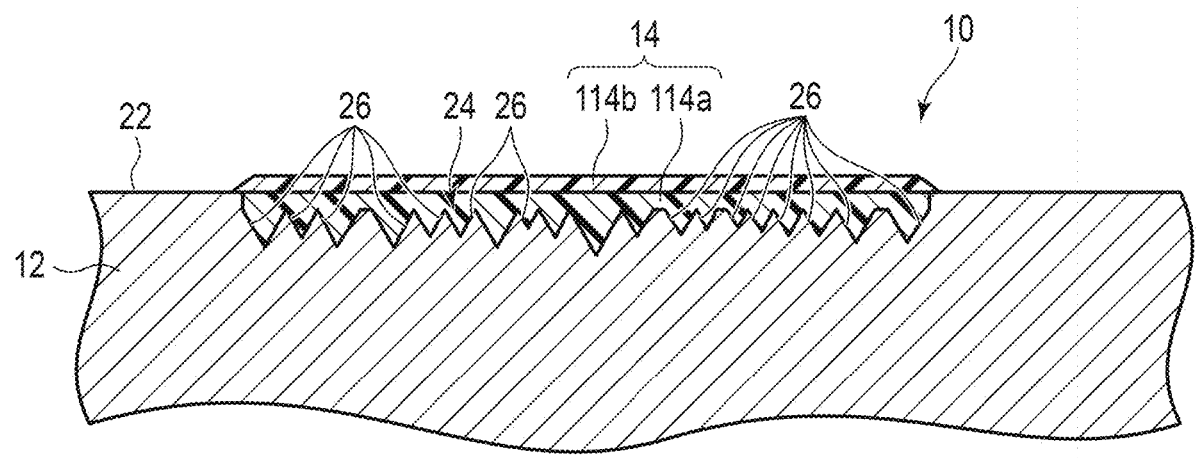
FIG. 15 is a schematic longitudinal sectional view showing a state in which a covering is formed on a metallic component used for a medical instrument according to a second embodiment.

As shown in FIG. 15, this example is applied to form the coating 14 by a plurality of layers, such as two layers. Here, the covering 14 has an inner side layer 114a that is in direct contact with the metallic component 12, and an outer side member 114b that is formed on the surface. In this case, in addition to appropriately selecting a material for the metallic component 12 and the outer side member 114b, a material of the inner side layer 114a is appropriately selected. For the inner side layer 114a, a material that is capable of obtaining desired adhesion between the metallic component 12 and the inner side layer 114a using the technique explained in the first embodiment, and that is capable of obtaining desired adhesion between the inner side layer 114a and the outer side member 114b is used. Therefore, even if there is incompatibility in the adhesion between the outer side member 114b and the metallic component 12, by arranging an appropriate inner side layer 114a between the metallic component 12 and the outer side member 114b, the covering 14 achieving a desired function can be formed on a surface layer of the metallic component 12.

Here, an example of using the inner side layer 114a and the outer side member 114b as a plurality of layers for the covering 14 has been explained; however, the outer side member 114b does not necessarily have to be layered. It is also preferable that the inner side layer 114a is able to fix, for example, an appropriate resin material structure as the outer side member 114b. Therefore, the outer side member 114b can be formed in an appropriate shape.

In the case where the inner side layer 114a and the outer side member 114b are formed of a resin material, even if a large load is applied to the interface between the inner side layer 114a and the outer side member 114b, since both of them are formed of a resin material, there is less possibility of interfacial peeling. In this manner, adhesion can be easily enhanced significantly, and peeling off can be made more difficult than in the case of directly fixing the outer side member 114b to the metallic component 12.

Incidentally, as shown in FIG. 13, when the knob 80 is rotated around the longitudinal axis of the probe 78 in the treatment instrument 70 mentioned above, the rotation is transmitted to the probe 78 via the covering 14. Here, an ultrasonic vibrator 122 also rotates together.

FIG. 13 shows the piezoelectric element 92 and an electrode 94 to which a force is applied in accordance with the rotation of the knob 80 and a movement of a cord 84a of the ultrasonic vibrator unit 84 accompanying the displacement of the treatment instrument 70. When a surgery is ended, the vibrator unit 84 is removed from the main body 72, and is autoclave-sterilized. When doing so, a high temperature and pressure steam is sprayed on the vibrator unit 84. The vibrator unit 84 is covered with a shield 96 to prevent the piezoelectric element from coming in contact with the steam so that heat denaturation does not occur to the piezoelectric element 92 therein. The shield 96 is formed of a hard resin material, such as a PEEK material.

Since the PEEK material has electrical insulating properties, in order to generate vibration by driving the piezoelectric element 92 stored inside the shield 96, an electrode pin 98 that penetrates a wall of the shield 96 is provided as an electric contact that is connected to the outside of the shield 96. While preventing a gap from occurring between the outer periphery of the electrode pin 98 and the inner periphery of the hole of the shield 96 in order to prevent the steam from entering, the electrode pin 98 should be formed so as to not come off from the hole of the shield 96 even if an electric wiring positioned at the proximal end side moves by the operation of the main body 72 and pulls the cord 84a. Therefore, in the present embodiment, the above-mentioned technique is used to apply blast processing on the outer periphery of the electrode pin 98 that serves as the metallic component 12, apply the coating 14 before releasing stress, and form the shield 96 configured by a resin material with respect to the coating 14. In other words, the electrode pin 98 serving as the metallic component 12 comprises a distal end portion and a proximal end portion. The covering 14 is formed as the shield 96 that covers the piezoelectric element 92 electrically connected to the distal end portion of the electrode pin 98, and in which the distal end portion of the electrode pin 98 is provided. In other words, the piezoelectric element 92 and the distal end portion of the electrode pin 98 are arranged in the shield 96. The proximal end portion of the electrode pin 98 is located outside the shield 96, and exposed to the outside of the shield 96. An end of a lead 98a arranged inside the cord 84a is connected to the proximal end portion of the electrode pin 98. Therefore, since the distal end portion of the electrode pin 98 is electrically connected to the piezoelectric element 92, and the proximal end portion of the electrode pin 98 is electrically connected to the lead 98a here, the covering 14 at least annularly covers the outer periphery of other than the distal end portion and the proximal end portion of the electrode pin 98. Furthermore, the shield 96 (outer side layer 114b) formed of a resin material, such as a PEEK material, is integrated or fused with a coating (inner side layer 114a) forming the covering 14 of the electrode pin 98, to ensure shielding properties of an interface between the shield 96 and the electrode pin 98.

The covering 14 on the outer periphery surface of the proximal end portion of the probe 78 shown in FIG. 14, that is, the inner side layer 114a, is integrated or fused with the inner periphery surface of the sheath 76, that is, the outer side layer 114b, to ensure a receiving/giving torque performance on the interface of the sheath 76 and the probe 78.

The cord 84a of the medical instrument 10 shown in FIG. 8 is moved to be connected to a power source that is not illustrated. The ultrasonic vibrator unit 84 connected to the cord 84a is reused after going through the process of being washed, disinfected, and sterilized after the medical instrument 10 is used. While sterilization, the ultrasonic vibrator unit 84 is exposed to high temperature and high pressure steam by, for example, an autoclave. The piezoelectric element 92 is covered by the shield 96. The shield 96 is formed of, for example, a hard resin material, such as a PEEK material.

The covering 14 can be appropriately used for medical instruments, such as a treatment instrument that uses an ultrasonic wave, a regular forceps, a monopolar type treatment instrument, a bipolar type treatment instrument, a treatment instrument that uses radio waves, and heat forceps. As mentioned above, the covering 14 is not limited to a resin material. The covering 14 such as a rubber material or a ceramic material, etc. that is used as a coating material can be used as appropriate.

In the first and second embodiments, the blast media 18 has been explained as being used for the surface processing with respect to the surface 22 of the metallic component 12. The surface processing is not limited to using the blast media 18, and can also be performed by using, for example, laser machining. The laser machining is also capable of forming a concave surface 24 that has a sharp-angled dent 26 with an appropriate depth with respect to the surface of the metallic component 12. Therefore, even by using the laser machining, the covering 14 can be formed appropriately with respect to the surface 22 of the metallic component 12 in the same manner as mentioned above.

After the covering 14 is formed on the metallic component 12, a publicly-known stress release using various low-temperature ranges may be performed. The stress release using a low-temperature range is performed by, for example, placing the metallic component 12 in a low temperature of about −200 degrees Celsius, then rapidly rising the temperature to about +100 degrees Celsius. A thermal shock caused by this processing prompts the release of the internal stress F of the metallic component 12. Therefore, the clutching force P for clutching the coating 14 by the concave surface 24 of the metallic component 12 can be further increased by the stress release using a low-temperature range.

Although not illustrated, about two to five times the adhesion strength was able to be obtained when a test was performed under the same conditions using the same materials as explained in the first embodiment with respect to the test specimen from which stress is released using a low-temperature range. Therefore, when stress release is performed using a low-temperature range, the covering 14 is several times more difficult to peel off in comparison to the covering 14 explained in the first embodiment.

The temperature for applying thermal shock by the stress release using a low-temperature range is selected as appropriate in accordance with the materials of the metallic component 12 and the coating 14 to be used. In summary, the temperature of the metallic component 12 on which the coating 14 is formed is increased rapidly from a temperature lower than 0 degrees Celsius towards a temperature higher than 0 degrees Celsius and lower than 300 degrees Celsius to apply thermal shock. Here, as explained above, for example, the coating 14 is several times harder to peel off, that is, several times more tolerant to a shear force, in comparison to the coating 14 explained in the first embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical instrument comprising:
a metallic component having a concave surface formed in a surface of the metallic component, the concave surface including a plurality of triangular recesses formed into the concave surface, the plurality of triangular recesses each being formed of a plurality of inner wall surfaces that are convex and protrude towards each other, and the plurality of inner wall surfaces of each respective triangular recess intersect at a bottom of the respective triangular recess; and
a covering that covers the concave surface while receiving a compressive force from the concave surface of the metallic component, wherein after the covering is applied to the concave surface to cover the plurality of triangular recesses, the plurality of inner wall surfaces of the plurality of triangular recesses are configured to transition from an initial shape, where the plurality of inner wall surfaces of each respective triangular recess are straight, to the convex shape, where the plurality of inner wall surfaces of each respective triangular recess protrude inward towards each other by the plurality of inner wall surfaces moving inward towards each other.

2. The medical instrument according to claim 1, wherein the covering is held on the concave surface by receiving the compressive force from the concave surface that is caused by a passage of time from forming the plurality of triangular recesses and by releasing internal stress of the metallic component by heat generated when forming the covering.

3. The medical instrument according to claim 1, wherein the metallic component includes a distal end portion and a proximal end portion, the metallic component having a longitudinal axis extending from the distal end portion to the proximal end portion, and the metallic component is configured to transmit vibration along the longitudinal axis.

4. The medical instrument according to claim 1, wherein the covering is integrated or fused with a resin material.

5. The medical instrument according to claim 1, wherein:
the metallic component includes a distal end portion and a proximal end portion, and the metallic component has a longitudinal axis extending from the distal end portion to the proximal end portion, and
the covering is configured to give or receive a rotational torque that at least rotates the metallic component around the longitudinal axis.

6. The medical instrument according to claim 1, wherein:
the metallic component is an electrode pin including a distal end portion and a proximal end portion, and
the covering is provided on a shield that annularly covers a part of the electrode pin, the distal end portion of the electrode pin and an electrical element electrically connected to the distal end portion of the electrode pin being arranged in the shield, the proximal end portion of the electrode pin being exposed to an outside of the shield and being electrically connected to a lead, and a coating forming the covering is integrated or fused with the shield to ensure shielding properties of an interface between the shield and the electrode pin.

7. The medical instrument according to claim 1, wherein:
the metallic component includes a distal end portion and a proximal end portion, and the metallic component has a longitudinal axis extending from the distal end portion to the proximal end portion, and
the covering is formed of at least a material having heat insulating properties, and the covering is arranged along the longitudinal axis.

8. The medical instrument according to claim 1, wherein:
the metallic component includes a distal end portion and a proximal end portion, and the metallic component has a longitudinal axis extending from the distal end portion to the proximal end portion, and the covering is formed of at least a material having electrical insulating properties, and the covering is arranged along the longitudinal axis.

9. The medical instrument according to claim 1, wherein:
the metallic component includes a distal end portion and a proximal end portion, and the metallic component has a longitudinal axis extending from the distal end portion to the proximal end portion, and
the covering is formed of at least a material having water repellency, and the covering is arranged along the longitudinal axis.

10. The medical instrument according to claim 1, wherein:
when the concave surface of the metallic component is formed, the concave surface is deformed by internal stress based on the compressive force from the concave surface of the metallic component; and
after the concave surface is formed, the covering covers the concave surface when the concave surface is deformed by the internal stress.

11. A manufacturing method of a covering with respect to a metallic component, the manufacturing method comprising: forming, in a surface of the metallic component, a concave surface by applying blast processing, the concave surface including a plurality of triangular recesses formed into the concave surface, the plurality of triangular recesses each being formed of a plurality of inner wall surfaces that are convex and protrude towards each other, and the plurality of inner wall surfaces of each respective triangular recess intersect at a bottom of the respective triangular recess; and
covering the concave surface by a covering material before an internal stress generated on the metallic component by forming the concave surface deforms and eliminates an opening formed on the surface by the concave surface in a manner to close the opening, wherein after the covering material is applied to the concave surface to cover the plurality of triangular recesses, the plurality of inner wall surfaces of the plurality of triangular recesses are configured to transition from an initial shape, where the plurality of inner wall surfaces of each respective triangular recess are straight, to the convex shape, where the plurality of inner wall surfaces of each respective triangular recess protrude inward towards each other by the plurality of inner wall surfaces moving inward towards each other.

12. The manufacturing method according to claim 11, further comprising applying a thermal shock by increasing a temperature of the metallic component on which the covering is covered from a temperature lower than zero degrees Celsius towards a temperature higher than zero degrees Celsius and lower than 300 degrees Celsius.

\* \* \* \* \*